(12) United States Patent
van Broeckhoven et al.

(10) Patent No.: US 7,960,117 B2
(45) Date of Patent: Jun. 14, 2011

(54) PROMOTER MUTATIONS THAT INCREASE AMYLOID PRECURSOR PROTEIN EXPRESSION

(75) Inventors: Christine van Broeckhoven, Edegem (BE); Jessie Theuns, Antwerp (BE)

(73) Assignees: VIB VZW, Zwijnaarde (BE); Universiteit Antwerpen, Antwerp (BE)

( * ) Notice: Subject to any disclaimer, the term of this patent is extended or adjusted under 35 U.S.C. 154(b) by 58 days.

(21) Appl. No.: 12/225,270

(22) PCT Filed: Mar. 12, 2007

(86) PCT No.: PCT/EP2007/052296
§ 371 (c)(1),
(2), (4) Date: Apr. 1, 2009

(87) PCT Pub. No.: WO2007/104739
PCT Pub. Date: Sep. 20, 2007

(65) Prior Publication Data
US 2009/0217395 A1    Aug. 27, 2009

(30) Foreign Application Priority Data
Mar. 16, 2006    (EP) .................................... 06111272

(51) Int. Cl.
*C12Q 1/68*    (2006.01)
*C07H 21/04*    (2006.01)

(52) U.S. Cl. .......................... 435/6; 536/24.3; 536/24.31

(58) Field of Classification Search ..... 435/6; 536/24.3, 536/24.31
See application file for complete search history.

(56) References Cited

FOREIGN PATENT DOCUMENTS

| GB | 2380196 | 4/2003 |
|---|---|---|
| WO | WO9640895 | 12/1996 |
| WO | WO 2007/104739 A1 | 9/2007 |

OTHER PUBLICATIONS

Lahiri et al., 2000, Molecular Brain Research, vol. 77, p. 185-198.*
Querfurth et al., 1999, Gene, vol. 232, p. 125-141.*
Rogaev et al., 1993, Neurology, vol. 43, p. 2275-2279.*
Athan et al., 2002, Arch Neurol, vol. 59, p. 1793-1799.*
Lahiri et al., Abstract, Characterization of two APP gene promoter polymorphisms that appear to influence risk of late-onset Alzheimer's disease. Neurobiology of Aging, Nov. 2005, pp. 1329-1341, vol. 26, No. 10, Tarrytown, NY, US.
Lahiri et al., Abstract, Promoter activity of the beta-amyloid precursor protein gene is negatively modulated by an upstream regulatory element, Molecular Brain Research, Jul. 23, 1999. pp. 32-41, vol. 71, No. 1.
Andra et al., Abstract, Expression of APP in transgenic mice: a comparison of neuron-specific promoters, Neurobiology of Aging, pp. 183-190, vol. 17, No. 2, Tarrytown, NY, US.
Howland et al.. Abstract, Mutant and native human beta-amyloid precursor proteins in transgenic mouse brain, Neurobiology of Aging, pp. 685-699, vol. 16, No. 4, Tarrytown, NY, US.
Lamb, et al., Abstract, Introduction and expression of the 400 kilobase precursor amyloid protein gene in transgenic mice, Nature Genetics, Sep. 1, 1993, pp. 22-29, vol. 5, NY, US.
Theuns, et al., Promoter mutations that increase amyloid precursor-protein expression are associated with Alzheimer disease. American Journal of Human Genetics, Jun. 2006, pp. 936-946, vol. 78, No. 6.
Lahiri et al., Characterization of two APP gene promoter polymorphisms that appear to influence risk of late-onset Alzheimer's disease, Neurobiology of Aging, Nov. 2005, pp. 1329-1341, vol. 26, No. 10, Tarrytown, NY, US.
Lahiri et al., Analysis of the 5'-flanking region of the beta-amyloid precursor protein gene that contributes to increased promoter activity in differentiated neuronal cells, Molecular Brain Research, May 5, 2000, pp. 185-198, vol. 77, No. 2, Elsevier Science BV, Amsterdam, NL.
Lahiri et al., Promoter activity of the beta-amyloid precursor protein gene is negatively modulated by an upstream regulatory element, Molecular Brain Research, Jul. 23, 1999, pp. 32-41, vol. 71, No. 1.
Andra et al., Expression of APP in transgenic mice: a comparison of neuron-specific promoters, Neurobiology of Aging, pp. 183-190, vol. 17, No. 2, Tarrytown, NY, US.
Howland et al., Mutant and native human beta-amyloid precursor proteins in transgenic mouse brain, Neurobiology of Aging, pp. 685-699, vol. 16, No. 4, Tarrytown, NY, US.
Lamb, et al., Introduction and expression of the 400 kilobase precursor amyloid protein gene in transgenic mice, Nature Genetics, Sep. 1, 1993, pp. 22-29, vol. 5, NY, US.
PCT International Search Report, PCT/EP2007/052296, dated May 25, 2007.

* cited by examiner

*Primary Examiner* — Shin-Lin Chen
(74) *Attorney, Agent, or Firm* — TraskBritt, P.C.

(57) ABSTRACT

The present invention relates to mutations in the amyloid precursor protein (APP) promoter region, whereby the mutations cause a significant increase in APP expression. The increase in APP expression is related to Alzheimer's disease, and the mutations can be used in Alzheimer's disease diagnosis, or in the construction of transgenic animal models for studying Alzheimer's disease.

7 Claims, 3 Drawing Sheets

PROMOTER MUTATIONS THAT INCREASE AMYLOID PRECURSOR PROTEIN EXPRESSION

CROSS-REFERENCE TO RELATED APPLICATIONS

This is a national phase entry under 35 U.S.C. §371 of International Patent Application PCT/EP2007/052296 filed Mar. 12, 2007, published in English as International Patent Publication WO 2007/104739 A1 on Sep. 20, 2007, which claims the benefit under Article 8 of the PCT of European Patent Application Serial No. 06111272.8 filed Mar. 16, 2006.

TECHNICAL FIELD

The present invention relates to mutations in the amyloid precursor protein (APP) promoter region, wherein the mutations cause a significant increase in APP expression. The increase in APP expression is related to Alzheimer's disease, and the mutations can be used in Alzheimer's disease diagnosis, or in the construction of transgenic animal models for studying Alzheimer's disease.

BACKGROUND

The currently most favored hypothesis advocates a pivotal role for the amyloid precursor protein in the molecular etiology of Alzheimer's disease. Clinical mutations in autosomal dominant AD were shown to increase relative concentrations of the 42 amino acids amyloid β (Aβ) peptide (Suzuki et al., 1994; Scheuner et al., 1996; Citron et al., 1997), a proteolysis product of APP, that shows increased propensity to aggregate (Burddick et al., 1992) and deposit in amyloid plaques in AD brains (Iwatsubo et al., 1994). Also, different missense mutations in the APP gene (APP) cause autosomal dominant early-onset familial AD (Goate et al., 1991) (Alzheimer Disease & Frontotemporal Dementia Mutation Database). Standard molecular diagnostic screening of APP is currently limited to exons 16 and 17—coding in part for the Aβ peptide—and their flanking splice sites. However, it is yet not excluded that genetic variation influencing transcriptional activity of APP might also contribute to disease risk. Aβ peptide production depends largely on the amount of APP substrate and, therefore, it is conceivable that regulation of APP transcription might indeed play an important role in AD susceptibility. In fact, several studies have identified higher levels of APP mRNA in AD brains (for a review, see Theuns and Van Broeckhoven, 2000), and increased expression of APP has been correlated with Aβ deposition in brain in instances such as severe head injury (Gentleman et al., 1993). Perhaps the most convincing evidence came from the observation that APP triplication in Down syndrome (DS) patients leads to an overexpression of APP (Rumble et al., 1989) and deposition of Aβ peptide in neuritic amyloid plaques (Wisniewski et al., 1985), resulting in a 50 year earlier onset of AD symptoms.

APP is expressed in a variety of tissues, with the highest expression levels in neuronal cells of the central nervous system (CNS), and can be induced by a variety of agents such as growth hormones and cytokines as well as stress conditions. Up-regulation of APP transcriptional activity (Siman et al., 1989; Sola et al., 1993) corroborated with the mRNA expression studies (Wirak et al., 1991; Lahiri and Nall, 1995), suggesting a major role for the APP promoter activity in APP expression. The proximal promoter region of APP is devoid of a functional TATA box, shows a high GC content and transcription initiation is regulated by a strong initiator element (Inr) surrounding the major transcription start site (TSS)+1 (Salbaum et al., 1988; La Fauci et al., 1989; Yoshikai et al., 1990; Quitschke et al., 1996). Further, APP promoter activation is mainly governed by two GC-rich elements, the −93/−82 fragment (APBβ) and the −65/−41 fragment (APBα) (Pollwein et al., 1992). Transcriptional activation of APP can also be mediated by heat-shock factor-1 (HSF-1) binding to the heat shock element (HSE) at position −317 following induction by numerous stress factors (Dewji and Do, 1996). Another transcriptional activator was mapped to −350/−366 harboring an AP-1 binding site and flanking the GC box (Querfurth et al., 1999). Of further interest is that members of the NFκβ/Rel family can specifically recognize two identical sequences at −2250/−2241 and −1837/−1822, in the distal promoter region of APP, referred to as APPκβ sites (Grilli et al., 1995). Both the expression patterns and the proximal promoter region of APP are highly conserved between mammalian species ($\geq$80%) (Yamada et al., 1989; Izumi et al., 1992; Chernak, 1993; Song and Lahiri, 1998).

Linkage and association studies support that genetic variability at the APP locus might contribute to increased risk for late-onset AD (Pericak-Vance et al., 1991; Kehoe et al., 1999; Wavrant-DeVrieze et al., 1999; Olson et al., 2002; Meyers et al., 2002; Blaker et al., 2003), in the absence of coding mutations (Lidell et al., 1995). These genetic data further suggested that increased susceptibility might result from genetic mutation in the 5' regulatory region of APP. However, early on screenings of the APP promoter in sporadic and familial early- and late-onset AD patients, did not reveal AD-specific mutations (Lidell et al., 1995; Fidani et al., 1992; Rooke et al., 1992; Rogaev et al., 1993). More recent studies detected a mutation of G to C at position +37 (hereinafter +37G>C) polymorphism in APP exon 1 while sequencing the −573/+125 fragment of the APP promoter in 20 individuals (Athan et al., 2002). The +37 C-allele was overrepresented in patients with late-onset AD lacking apolipoprotein E (APOE) ε4 alleles (17.2%) compared to elderly control individuals (10%) (OR 2.08, CI 1.26-3.45, adjusted for age, gender and education). Subsequent sequencing of the −308/+124 fragment in 173 patients with late-onset AD and 840 control individuals revealed one more rare variant in control individuals, −9G>C (0.7%), but absent in AD patients. However, both variants, −9G>C and +37G>C, showed no allelic differences in promoter activity when tested in U-87 glioma cells using a reporter gene assay.

The APP locus is known to be complex with several other active sites in the 5' regulatory region apart from the core promoter. In fact, functional elements that control activity of the human APP promoter are located in three distal regions −2257/−2234, −2250/−2241 and −1837/−1822. Constructions in which the distal region −2435/−2165 has been removed showed an increase in promoter activity (Lahiri et al., 1999). However, this large deletion is not occurring in Alzheimer patients, and no Alzheimer disease-related mutations could be found in this region.

DISCLOSURE OF THE INVENTION

Surprisingly, we found several point mutations in the proximal promoter region that cause a significant increase in expression of APP. These mutations occur only in Alzheimer's disease patients and are clearly associated with the disease.

A first aspect of the invention is a mutation in the regulatory region of the amyloid precursor protein gene resulting in at least a 1.2 times increase in amyloid precursor protein expression, preferably a 1.5 times increase in APP expression as compared with wild-type expression. For the use in this application, increase in amyloid expression is measured as luciferase activity, after transfection of APP-promoter luciferase reporter constructs in human SH-SY5Y neuroblastoma cells, as described in the materials and methods to the examples. The regulatory region of the APP gene, as used herein, consists of the region −5529 till +204 of SEQ ID NO:1 (Lahiri, 2004). Preferably, the regulatory region is limited to the region −2257 till +204. Most preferably, the mutation is situated in the APP proximal promoter region (−766/+204). A mutation as used herein is limited to mutations that can be found in patients. Preferably, the mutation is a small deletion (less than ten nucleotides), an insertion such as a partial duplication within the regulatory region, or a point mutation. Even more preferably, the mutation is a point mutation. More preferably, the mutation is selected from the group consisting of −118C>A, −369C>G, −479C>T and −534G>A. Most preferably, the mutation is selected from the group consisting of −118C>A, −369C>G and −534G>A.

Another aspect of the invention is the use of a mutation according to the invention in diagnosis of Alzheimer's disease. Any method capable of detecting the mutation can be used. Methods to identify the mutation in patient material are known to the person skilled in the art and include, but are not limited to, PCR amplification, sequencing and hybridization.

Still another aspect of the invention is the use of a mutation according to the invention in the construction of a cell line. The cell line will be overproducing APP and can be used to study the amyloid formation and/or to test compounds preventing amyloid formation.

Still another aspect of the invention is the use of a mutation according to the invention in the construction of a non-human transgenic animal. Indeed, introduction of a mutation according to the invention in a model organism such as a mouse would lead to an increase of APP production and development of an Alzheimer's disease-like phenotype. Methods to make mutant APP-based transgenic animals have been described, amongst others, in GB2380196 and in WO9640895. Such model organisms could be used for screening compounds and testing medication useful for treatment of Alzheimer's disease.

DETAILED DESCRIPTION OF THE INVENTION

EXAMPLES

Materials and Methods to the Examples

Patient-Control Groups

Figure 1:
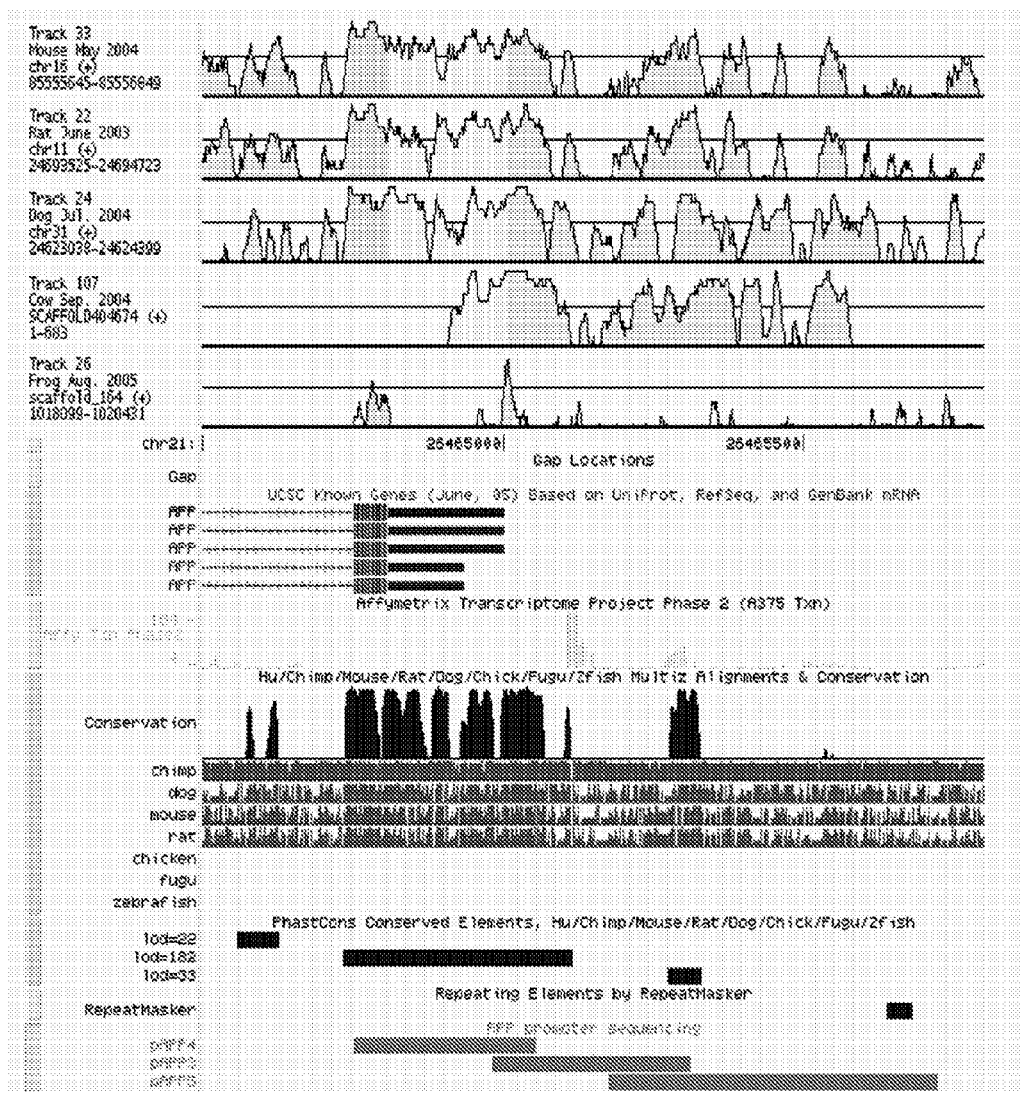
FIG. 1: Conservation plot of the APP 5' upstream region. Plots were generated using the VISTA Browser software and tracks were presented on the UCSC browser (Frazer et al., 2004). Conserved regions are defined as regions with a conservation score 50% or higher that are larger than or equal to 20 bp. Horizontal black lines crossing the conservation plots mark the 70% conservation boundary. Regions of high conservation are colored according to the annotation as exons (dark blue), UTRs (light blue) or non-coding sequences (pink).

AD patients (N=180) and control individuals from the Dutch-speaking Flanders region in Belgium were derived from a prospective study of dementia (Engelborghs et al., 2003; Engelborghs et al., 2006), whereas Dutch patients (N=111) and control individuals were ascertained in a population-based study of early-onset AD in the four northern provinces of The Netherlands and the area of metropolitan Rotterdam. The patients were sampled during two study periods. The original sample was collected between 1980 and 1987 (Hofman et al., 1989) and was extended between 1997 and 2000 in a genetically isolated part of the previously described area with the same sampling criteria (Dermaut et al., 2003). Main characteristics of these study samples are summarized in Table 1. Dutch patients were diagnosed with probable AD before 65 years. Belgian AD patients were included till an onset age of 70 years; 80 patients had an onset age of ≦65 years. Clinical diagnosis of probable AD was based on consensus by at least two neurologists in the Belgian study, or a neurologist and a member of the research team in the Dutch study, according to the National Institute of Neurological and Communicative Disorders and Stroke-Alzheimer's Disease and Related Disorders Association criteria (McKhann et al., 1984). For all patients, detailed data on family history of dementia in first-, second-, and third-degree relatives were collected by interviewing a next of kin of the patient. The criterion we used for familial patients was at least one first-degree relative with dementia. The criteria for autosomal dominant inheritance were (1) at least three patients with clinically diagnosed AD in two or more generations and (2) detailed medical records available on the clinical diagnosis of AD in at least two affected relatives.

TABLE 1

Characteristics of Belgian and Dutch early-onset AD study groups

|  | Belgian sample | | Dutch sample | |
| --- | --- | --- | --- | --- |
|  | AD | Control subjects | AD | Control subjects |
| Number | 180 | 180 | 111 | 270 |
| Mean AAO/AAI ± SD (years) | 63.8 ± 5.9 | 59.2 ± 16.7 | 56.1 ± 5.5 | 57.5 ± 2.8 |
| Female (%) | 55 | 56 | 76 | 60 |
| Familial AD (%) | 41.5 | n.a. | 69 | n.a. |

Note:
AAO, age at onset;
AAI, age at inclusion;
SD, standard deviation;
n.a., not applicable;
"familial" was defined as having at least one affected first degree relative.

Belgian (N=180) and Dutch (N=270) control individuals had no neurological or psychiatric antecedents and consisted of subjects without organic disease involving the central nervous system based on clinical examination. Genomic DNA of patients was systematically screened for mutations in the coding exons of four dementia genes PSEN1 [MIM 104311], PSEN2 [MIM 600759], MAPT [MIM 157140] and PRNP [MIM 176640] and exons 16 and 17 of APP [MIM 104760]. We identified putative causal missense mutations in eight Belgian patients (4%, i.e., four in PSEN1, three in PSEN2 and one in APP (Brouwers et al., unpublished data)), and in seven Dutch patients (6%, five in PSEN1 and two in PSEN2) (Dermaut et al., 2003; Cruts et al., 1998).

Sequence Analysis of the APP 5' Regulatory Region

The proximal promoter region of APP (−766/+204) was amplified by PCR using three overlapping primer sets: APP-766F (5'-cccccgccccgcaaaatc-3' (SEQ ID NO:2)) and APP-218R (5'-tgggcttcgtgaacagtgggagggagag-3' (SEQ ID NO:3)) APP-356F (5'-atgattcaagctcacggggacgag-3' (SEQ ID NO:4)) and APP-25R (5'-gctcagagccaggcgagtcagc-3' (SEQ ID NO:5)), APP-99F (5'-ggcggcgccgctagggggtctct-'3 (SEQ ID NO:6)) and APP+204R (5'-ctccagcgcccgagccgtccag-3' (SEQ ID NO:7)). The distal promoter fragments (−2634/−2159 and −2096/−1563) were amplified using two additional primer sets: APP-2634F (5'-gacgcaatcagcagcataatca-3' (SEQ ID NO:8)) and APP-2159R (5'-ctgggaaggaggaggcaact-3' (SEQ ID NO:9)), APP-2096F (5'-catgcttggtttaacgctctgc-3' (SEQ ID NO:10)) and APP-1563F (5'-gttcactttctgcaccacatttacc-3' (SEQ ID NO:11)). Oligonucleotide primers for PCR amplification of the APP promoter were based on Genbank D87675.1. Numbering is relative to the major TSS +1 at nt 9001 in D87675.1. About 20 ng genomic DNA were amplified in a total reaction volume of 25 μl containing 10 pmol of each primer, 0.2 mM dNTPs (dATP, dCTP, dTTP) (Amersham, Buckinghamshire, UK), 0.5 mM 7-Deaza-dGTP (Amersham), 0.5 U Platinum or Titanium Taq DNA polymerase (Invitrogen, Carlsbad, Calif. USA) and 1× Platinum/Titanium Taq reaction buffer. Further reaction conditions were thoroughly optimized for each primer set (available upon request). PCR products were screened for mutations by direct sequencing using BigDye® Terminator v3.1 Cycle Sequencing Kit (Applied Biosystems, Foster City, Calif.) on the ABI3730 automated DNA sequencer (Applied Biosystems) using the PCR primers. Sequences were analyzed using the NovoSNP software (Weckx et al., 2005). Each of the variations was confirmed by RFLP or pyrosequencing (Table 2) in the respective carriers. To screen 450 age- and gender-matched healthy controls, we used deaza-sequencing to detect the variations located between −766 and −218 and pyrosequencing assays for the remaining variations (Table 2). Due to the high GC content of the APP promoter, it was necessary to perform a nested PCR with the pyrosequencing primers on the respective promoter PCR products.

MatInspector (Quandt et al., 1995) was applied to investigate the effect of the variations on putative transcription factor binding sites using a core similarity cut-off value of 0.75 and an optimized matrix similarity threshold. Conserved sequences were detected using the VISTA tools.

TABLE 2

Mutation detection assays.

| Variation | PCR primers | Pyrosequencing/Sequencing primers |
|---|---|---|
| −2335 C>T | 5'-gacgcaatcagcagcataatca-3' (SEQ ID NO: 12)<br>5'-ctgggaaggaggaggcaact-3' (SEQ ID NO: 14) | 5'-bio-gatctcggctcacttcaagc-3' (SEQ ID NO: 13)<br>5'-aaattagccgggcgtcgt-3' (SEQ ID NO: 15)<br>5'-gtagtcccagctac-3' (SEQ ID NO: 16) |
| −1901G>T | 5'-catgcttggtttaacgctctgc-3' (SEQ ID NO: 17)<br>5'-gttcactttctgcaccacatttacc-3' (SEQ ID NO: 19) | 5'-attctcctgcctcagcctct-3' (SEQ ID NO: 18)<br>5'-bio-gtgaaaccccatctctactaaaaat-3' (SEQ ID NO: 20)<br>5'-gctgggattacaggca-3' (SEQ ID NO: 21) |
| −1750G>A | 5'-catgcttggtttaacgctctgc-3' (SEQ ID NO: 22)<br>5'-gttcactttctgcaccacatttacc-3' (SEQ ID NO: 24) | 5'-bio-cctgacctcaggtgatctgc-3' (SEQ ID NO: 23)<br>5'-gcaaacgtgagaccctttgt-3' (SEQ ID NO: 25)<br>5'-attattaagaattttaaggc-3' (SEQ ID NO: 26) |
| −534G>A | | 5'-gaaattccaggttgctcgtg-3' (SEQ ID NO: 27)<br>5'-bio-ggcgtttctggaagagaatg-3' (SEQ ID NO: 28)<br>5'-gggggttaaaaaatgag-3' (SEQ ID NO: 29) |
| −479C>T | | 5'-ctgtctcaacaagcaaagaaaatcct-3' (SEQ ID NO: 30)<br>5'-bio-gtggggcaggcgtttctg-3' (SEQ ID NO: 31)<br>5'-ttaagcttcactcgtt-3' (SEQ ID NO: 32) |
| −371G>A, −369C>G | 5'-cccccgccccgcaaaatc-3' (SEQ ID NO: 33)<br>5'-tgggcttcgtgaacagtgggagggagag-3' (SEQ ID NO: 35) | 5'-cccccgccccgcaaaatc-3' (SEQ ID NO: 34)<br>5'-tgggcttcgtgaacagtgggagggagag-3' (SEQ ID NO: 36) |

TABLE 2-continued

Mutation detection assays.

| Variation | PCR primers | Pyrosequencing/Sequencing primers |
|---|---|---|
| −118C>A | 5'-atgattcaagctcacggggacgag-3' (SEQ ID NO: 37) 5'-gctcagagccaggcgagtcagc-3' (SEQ ID NO: 39) | 5'-bio-agggcgctgcacctg-3' (SEQ ID NO: 38) 5'-ctcggcacccgagaga-3' (SEQ ID NO: 40) 5'-gaactgcgcccgct-3' (SEQ ID NO: 41) |
| +37G>C | 5'-ggcggcgccgctaggggtctct-3' (SEQ ID NO: 42) 5'-ctccagcgcccgagccgtccag-3' (SEQ ID NO: 44) | 5'-bio-gggctccgtcagtttcct-3' (SEQ ID NO: 43) 5'-ccgcgtccttgctctg-3' (SEQ ID NO: 45) 5'-gggcccccgcgca-3' (SEQ ID NO: 46) |

−371G/A and −369C/G were detected by sequencing and confirmed by StuI RFLP. For all other variations, a Pyrosequencing assay was designed.

Luciferase Reporter Gene Constructs

Genomic fragments of the APP proximal promoter were obtained by PCR amplification of DNA of patients or asymptomatic mutation carriers using the APP−766F and APP+204R primers as described above and cloned into the pCR2.1-TOPO vector (Invitrogen). The integrity of all inserts was confirmed by sequence analysis using the BigDye® Terminator v3.1 Cycle Sequencing Kit (Applied Biosystems, Foster City, Calif.) using vector-specific primers. Mutant clones were selected and consequently recloned into the promoterless pGL3 basic vector (Promega) upstream of the firefly luciferase gene, using KpnI and XhoI.

Transient Transfection in Cultured Mammalian Cells

Human SH-SY5Y neuroblastoma cells were propagated in a minimal essential medium with Earle's salt, 10% fetal bovine serum, 2 mM L-glutamine, 200 IU/ml of penicillin, 200 g/ml of streptomycin and 0.1 mM nonessential amino acids (Invitrogen). Human HEK293 embryonic kidney cells were propagated in OptiMem (Invitrogen) with 10% fetal bovine serum, 200 IU/ml of penicillin and 200 g/ml of streptomycin. For transient transfection, SH-SY5Y and HEK293 cells were seeded in 24-well tissue culture dishes, at $7.5 \times 10^5$ and $6 \times 10^5$ cells/well, respectively, and allowed to recover for 24 hours. Cells were co-transfected with 32 ng (HEK293) or 80 ng (SH-SY5Y) of pRL-TK plasmid containing the herpes simplex virus thymidine kinase promoter upstream of the *renilla* luciferase gene (Promega) and 800 ng of either one of the APP promoter constructs or one of the control plasmids, using 2.4 μl Lipofectamine 2000 (Invitrogen). Empty pGL3-basic vector was used as a negative control, pGL3-promoter plasmid containing the SV40 early promoter upstream of the firefly luciferase gene (Promega) as a positive control.

Luciferase Activity

Transfected cells were cultured for 24-36 hours, washed with 1 ml phosphate-buffered saline (PBS, Invitrogen), and lysed with Passive lysis buffer (Promega). Firefly luciferase activities ($LA_F$) and *renilla* luciferase activities ($LA_R$) were measured sequentially using a Dual-Luciferase reporter assay system (Promega) and a Veritas™ Microplate Luminometer with Dual Reagent Injectors Luminometer (Promega). To correct for transfection efficiency and DNA uptake, the relative luciferase activity (RLA) was calculated as $RLA=LA_F/LA_R$.

Electrophoretic Mobility Shift Assays

Nuclear factors were extracted from SH-SY5Y cells using the NucBuster Protein Extraction Kit (Novagen). DIG-labeled single-stranded oligonucleotides of 31 bp spanning each variant of APP −534G/A, −369C/G and −118C/A were designed and HPLC purified. Blunt-ended double-stranded probes were obtained by annealing of the specific oligonucleotides with their respective reverse complements and checked on a non-denaturing 15% polyacrylamide gel in 0.25×TBE. For the binding reactions, 200 fmol DIG-labeled double-stranded probe was added to a total reaction volume of 20 μl containing 10 μg SH-SY5Y nuclear extract, 1× binding buffer (12% glycerol, 20 mM HEPES or TRIS, 50 mM KCl, 1 mM EDTA, 1 mM DTT, 1 mM PMSF) and 1 μg poly (dI-dC) (Roche Applied Science). For competition assays, unlabeled double-stranded probes were added to the reaction mixture prior to addition of the labeled probe. Binding reactions were incubated at room temperature for 20 minutes. Protein-DNA complexes were analyzed by electrophoresis on non-denaturing 6% polyacrylamide gels in 0.25×TBE and visualized by chemiluminescent detection using the DIG gel shift kit (Roche Applied Science).

Real-Time PCR mRNA Quantification mRNA was isolated from cultured lymphoblast cells of mutation carriers and control individuals using the mRNA Chemagic isolation system (Chemagen, Baesweiler, Germany) and first strand cDNA was synthesized from 300 ng of mRNA using the SuperScript™ III First-Strand Synthesis System for RT-PCR (Invitrogen). APP expression levels were quantified using a Taqman-MGB real-time PCR assay on the ABI Prism 7900HT Sequence Detection System (Applied Biosystems). Primers and probes were designed with the PrimerExpress software (Applied Biosystems) and sequences are available upon request. Human APP mRNA quantities were normalized for the three housekeeping genes, ubiquitine C (hUBC), β2-microglobulin (hB2M) and tyrosine 3-monooxygenase/tryptophan 5-monooxygenase activation protein, zeta polypeptide (hYWHAZ (SEQ ID NO:47)) as recommended by Vandesompele et al. (2002). 1/20 fold-diluted cDNA was amplified in a 20 μl reaction containing 1×qPCR Mastermix Plus (no UNG) (Eurogentec, Seraing, Belgium), 300 nM primers and 250 nM probe using the universal amplification protocol (Applied Biosystems).

Statistical Analysis

The Mann-Whitney U test, a nonparametric analogue to the unpaired t test, was used to compare the RLA produced by the wild-type and mutant transfectants, as well as real-time PCR quantifications of APP expression levels.

Example 1

Variation in the 5' Regulatory Region of APP

We sequenced the −766/+204 region of the proximal APP promoter and exon 1, and two more distal promoter regions −2634/−2159 and −2096/−1563, in two independently ascertained Dutch-speaking early-onset AD groups composed of 180 Belgian and 111 Dutch patients (Table 1). In total, we identified nine heterozygous sequence variants and confirmed their presence in the respective carriers by a second method, i.e., PCR-RFLP analysis or pyrosequencing (Table 3—Quandt et al., 1995; Brouwers et al., 2006). Analysis in 450 age- and gender-matched healthy control individuals (180 Belgian and 270 Dutch individuals) demonstrated that three variants (33%) were known polymorphisms: −2335C/T (rs364091), −1901G/T (rs1235879) and +37G/C (rs459543) (Table 3A), the latter being the same one reported by Athan et al., (2002). Also, in agreement with this study, the −9G>C variant was not observed in the AD patients. Six of nine variations (67%) were present in patients only (Table 3B). One Dutch patient, d807, with onset age 50 years was compound heterozygote for two promoter mutations −1750G>A and −118C>A.

suggestive for a potential common ancestor, though the shared haplotype had a frequency of 1% in control individuals.

Recently, we obtained autopsied brain material of the Belgian AD patient carrying the APP (−369G>C) promoter mutation and a detailed neuropathological examination is in progress. Structural brain imaging of this patient during the disease progress, however, revealed white matter lesions reminiscent of those found in APP duplication carriers, suffering from AD with pronounced CAA due to overexpression of APP.

Another familial Dutch patient, d786, carried the −534G>A mutation. In two Belgian patients, d4605 and d5165, with onset ages 55 and 62 years, the −371G>A and −479C>T mutations were identified, respectively. Neither one of the familial patients fulfilled our criteria for autosomal dominant AD.

TABLE 3

Sequence variants in the APP 5' regulatory region. A. Common variants; B. Early-onset AD patients; and C. Control individuals.

A.

| Variation[1] | Frequency (controls) | TF binding alterations[2] (core/matrix similarity) |
|---|---|---|
| −2335 C/T | 4% | No matches |
| −1901 G/T | 4% | +PAX-6 (0.75/0.75) |
|  |  | +FKHD (0.75/0.79) |
| +37 G/C | 4% | +CDEF (1/0.87) |

B.

| Variation[1] | Patient ID | Nationality | Onset age (years) | Current or age at *death (years) | Family history | APOE[4] | TF binding alterations[2] (core/matrix similarity) |
|---|---|---|---|---|---|---|---|
| −1750G > A[3] | d807 | Dutch | 50 | *64 | − | 34 | No major changes |
| −534G > A | d768 | Dutch | 52 | *70 | + | 34 | +OCT-1 (0.89/0.92) |
| −479C > T | d5165 | Belgian | 62 | *69 | − | 33 | −GAGA (0.750/0.789) +OCT-1 (0.771/0.843) |
| −371G > A | d4605 | Belgian | 55 | 64 | − | 33 | −AP2 (0.976/0.916) −STAF (0.904/0.799) |
| −369C > G | d811 | Dutch | 63 | *? | + | 34 | −AP-2 (1/0.92) |
|  | d1081 | Belgian | 61 | 75 | + | 44 |  |
| −118C > A[3] | d807 | Dutch | 50 | *64 | − | 34 | −AP-2 (1/0.91) −HES-1 (0.83/0.92) |

C.

| Variation[1] | ID | Age at inclusion (years) | APOE[4] | TF binding alterations[2] (core/matrix similarity) |
|---|---|---|---|---|
| −375G > C | d3155 | 56 | 33 | +SP1 (1/0.915) |
| −343A > C | d3099 | 56 | 33 | No alterations |

Note:
[1]Position relative to the major APP transcription start site (Inr) at nt. 9001 in GenBank accession number D87675.1;
[2]Matinspector analysis (Quandt et al., 1995);
[3]Patient d807 is compound heterozygous for these mutations;
[4]APOE was genotyped as previously described (Brouwers et al., 2006).

One other mutation, −369C>G, was identified in two familial patients, d811 (Dutch) and d1081 (Belgian), with very similar onset ages of 63 and 61 years, respectively. Haplotype analysis in these patients identified shared alleles at five neighboring microsatellite markers in the 210 kb APP region To investigate to what extent genetic variability in the APP promoter was patient-related, we sequenced the −766/+204 proximal promoter region in 48 control individuals. We identified only two additional rare polymorphisms, −343A>C and −375G>C, that were each present in one control individual (Table 2C). Also, since four of the six mutations identified in patients were located in the −766/−218 region, we sequenced this 548 bp region in all 450 control individuals but did not detect any additional variants.

Example 2

Transcriptional Activity of APP Promoter Mutations

Figure 2:
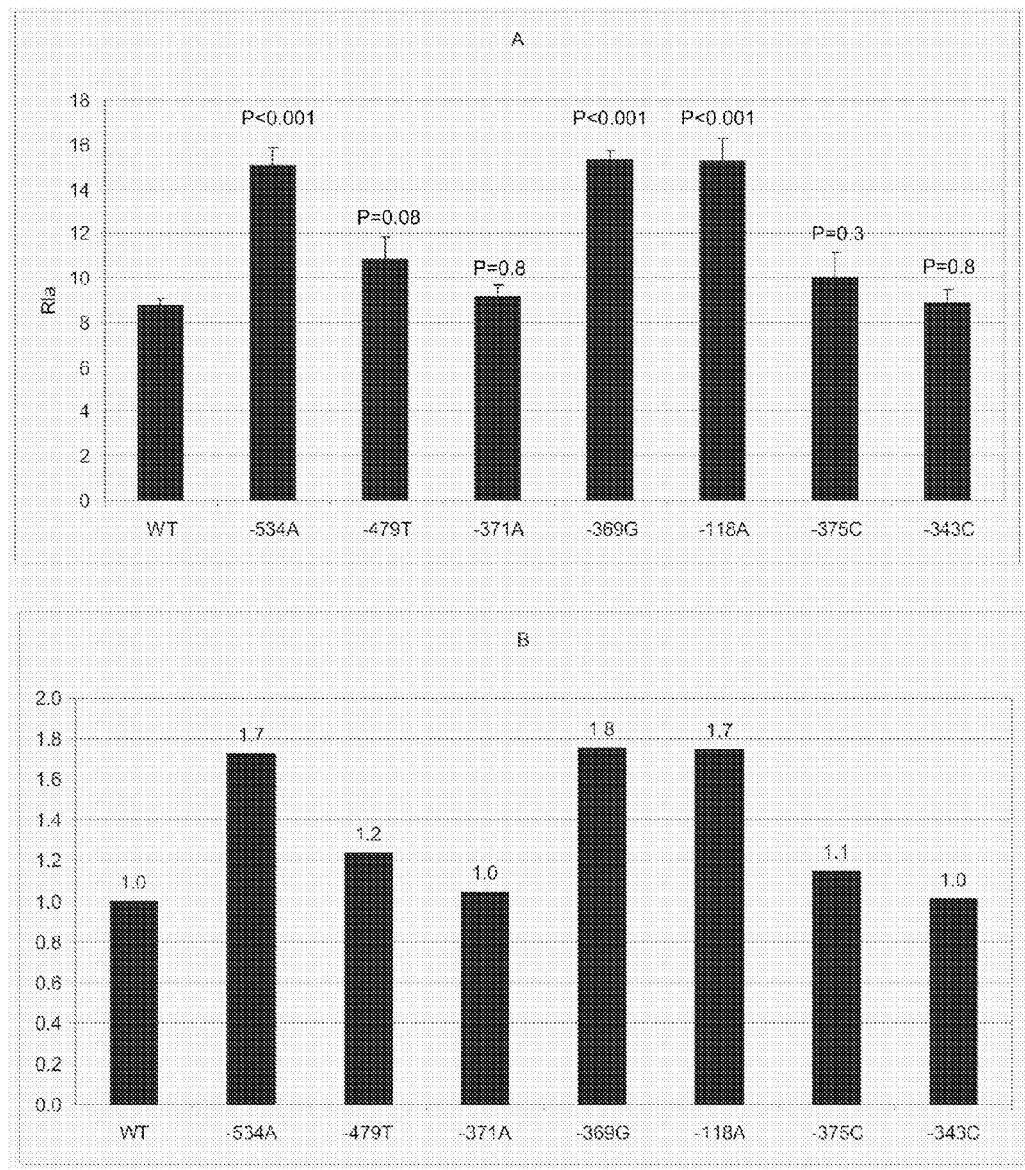
FIG. 2: Transcriptional activity of APP promoter variants. Panel A: Bars represent firefly/*renilla* luciferase ratios for the different constructs (relative luciferase activity, RLA). Values are mean±SEM of at least eight independent measurements. The significance of differences in expression was calculated using the Mann-Whitney U test and p-values are presented above the bars. Panel B: Relative increase of APP promoter activity compared to WT.

We cloned the −766/+204 APP promoter fragment containing wild-type (WT), or mutant −534A, −479T, −371A, −369G, or −118A alleles into the pGL3basic vector upstream of a firefly luciferase reporter gene. As controls, we used the −375C and −343C alleles, identified in control individuals. Reporter gene assay of transiently transfected human embryonic kidney (HEK293) cells showed no significant differences in expression level between −534A, −479T, −371A, −369G, and −118A and WT promoter sequences. Also, real-time PCR APP mRNA quantification in lymphoblasts from the mutation carriers (N=2) did not reveal significant differences in expression levels compared to control individuals. However, in human neuroblastoma (SH-SY5Y) cells, a significant near two-fold increase (p-value<0.001) in APP transcriptional activity was observed for three of the five mutant alleles identified in early-onset AD patients: −534A, −369G and −118A (FIG. 2). The other two mutant alleles, −479T and −371A, did not significantly increase transcriptional activity (p=0.08 and p=0.8, respectively). Neither one of the two variant alleles found in control individuals significantly altered transcriptional activity of the APP promoter in either one of the studied cell types (FIG. 2).

The neuron-specific doubling of expression found caused by the point mutations in the proximal part of the APP promoter is comparable to the increased level of APP expected from the genomic APP triplication in DS patients. Therefore, one can conclude that these promoter mutations also cause a critical elevation of APP in vivo in the AD patients. The reliability of our findings is supported by the fact that all mutation carriers had a follow-up diagnosis of probable AD. Further, in the Belgian prospective study, we observed 100% (N=55), and in the Dutch study, 88% (N=17), correlation with pathological diagnoses in probable AD patients. Also, quantification by ELISA of the abundance of amyloid β, tau and phosphotau in the cerebrospinal fluid (CSF) of two Belgian APP mutation carriers showed a decrease of Aβ42 and a slight increase of tau and phospho-tau typical for AD.

Example 3

Allele-Specific Transcription Factor Binding

Figure 3:
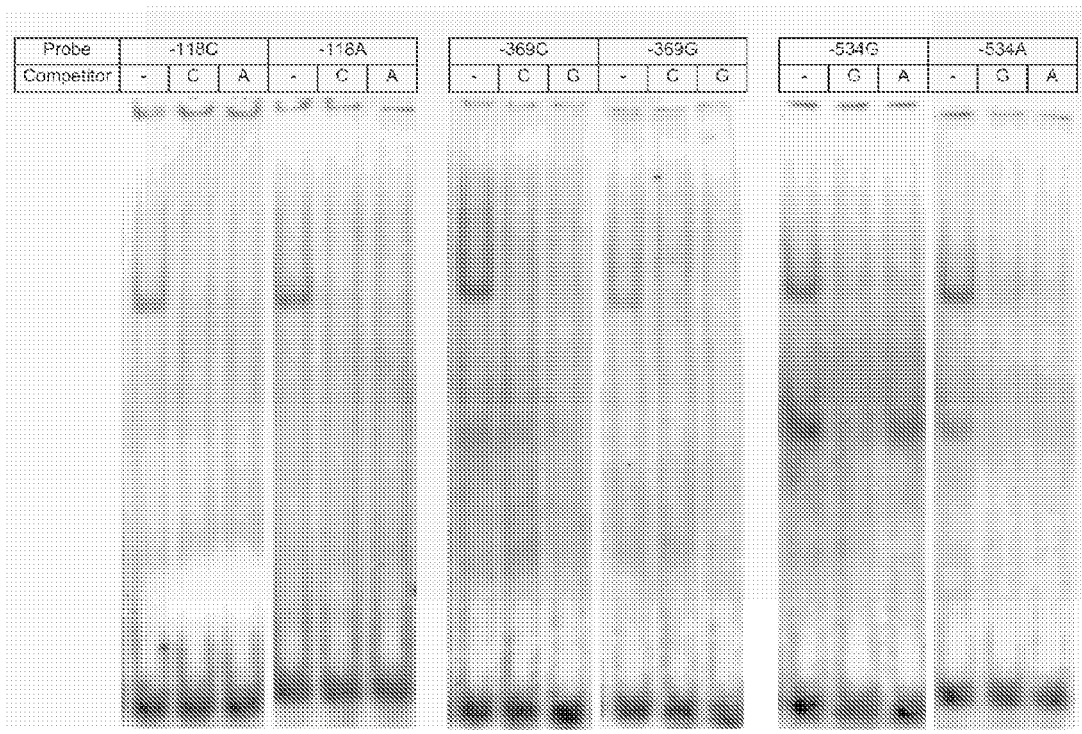
FIG. 3: Allele-specific binding of transcription factors. EMSA analysis of allele-specific effect of A) −118C/A, B) −369C/G, and C) −534G/A on the interaction of nuclear protein complexes extracted from SH-SY5Y cells. DIG-labeled double-stranded probes (200 fmol) were incubated with 10 µg nuclear extract from SH-SY5Y cells. In competition experiments, a 50-fold excess of unlabeled probe was added prior to the addition of the labeled probes.

We examined whether the three mutant alleles affecting APP expression (−118C/A, −369C/G, −534G/A) interfered with the specific recognition of the APP promoter by nuclear factors extracted from SH-SY5Y cells using electrophoretic mobility shift assays (EMSA). We used 31 bp long double-stranded oligomers containing one of six possible promoter alleles. We observed that SH-SY5Y nuclear extracts contained nuclear proteins binding specifically to all three regions of the APP promoter, resulting in the formation of one or two major complexes (FIG. 3). Competition with 50-fold excess of the respective unlabeled oligomers resulted in complete inhibition of complex formation. For −118C/A, one major complex bound to both alleles, however, with a higher binding affinity for the mutant A-allele. The major complex binding to the −369C/G probe showed a decrease in binding affinity or even a slight shift in complex mobility for the mutant G-allele. Two major complexes were formed on the oligomers of the −534G/A variant, however, with clear differences in binding affinity for the faster migrating complex, which preferentially bound to the WT G-allele. Also, competition with a 50-fold excess of cold −534A oligomer did not completely inhibit binding of the smaller complex to the −534G allele supporting the hypothesis of higher binding affinity of this complex for the G-allele.

REFERENCES

1. Athan E. S., J. H. Lee, A. Arriaga, R. P. Mayeux, and B. Tycko (2002). Polymorphisms in the promoter of the human APP gene: functional evaluation and allele frequencies in Alzheimer disease. *Arch. Neurol.* 59:1793-1799.
2. Blacker D., L. Bertram, A. J. Saunders, T. J. Moscarillo, M. S. Albert, H. Wiener, R. T. Perry, J. S. Collins, L. E. Harrell, R. C. Go, A. Mahoney, T. Beaty, M. D. Fallin, D. Avramopoulos, G. A. Chase, M. F. Folstein, M. G. McInnis, S. S. Bassett, K. J. Doheny, E. W. Pugh, and R. E. Tanzi (2003). Results of a high-resolution genome screen of 437 Alzheimer's disease families. *Hum. Mol. Genet.* 12:23-32.
3. Brouwers N., K. Sleegers, S. Engelborghs, V. Bogaerts, C. M. van Duijn, P. P. De Deyn, C. Van Broeckhoven, and B. Dermaut (2006). The UBQLN1 polymorphism, UBQ-8i, at 9q22 is not associated with Alzheimer's disease with onset before 70 years. *Neurosci. Lett.* 392:72-74.
4. Burdick D., B. Soreghan, M. Kwon, J. Kosmoski, M. Knauer, A. Henschen, J. Yates, C. Cotman, and C. Glabe (1992). Assembly and aggregation properties of synthetic Alzheimer's A4/beta amyloid peptide analogs. *J. Biol. Chem.* 267:546-554.
5. Chernak J. M. (1993). Structural features of the 5' upstream regulatory region of the gene encoding rat amyloid precursor protein. *Gene* 133:255-260.
6. Citron M., D. Westaway, W. Xia, G. Carlson, T. Diehl, G. Levesque, K. Johnson-Wood, M. Lee, P. Seubert, A. Davis, D. Kholodenko, R. Motter, R. Sherrington, B. Perry, H. Yao, R. Strome, I. Lieberburg, J. Rommens, S. Kim, D. Schenk, P. Fraser, H. St. George, and D. J. Selkoe (1997). Mutant presenilins of Alzheimer's disease increase production of 42-residue amyloid beta-protein in both transfected cells and transgenic mice. *Nat. Med.* 3:67-72.
7. Cruts M., C. M. van Duijn, H. Backhovens, M. Van den Broeck, A. Wehnert, S. Serneels, R. Sherrington, M. Hutton, J. Hardy, P. H. St. George-Hyslop, A. Hofman, and C. Van Broeckhoven (1998). Estimation of the genetic contribution of presenilin-1 and -2 mutations in a population-based study of presenile Alzheimer disease. *Hum. Mol. Genet.* 7:43-51.
8. Dermaut B., E. A. Croes, R. Rademakers, B. M. Van den, M. Cruts, A. Hofman, C. M. van Duijn, and C. Van Broeckhoven (2003). PRNP Val129 homozygosity increases risk for early-onset Alzheimer's disease. *Ann. Neurol.* 53:409-412.
9. Dewji N. N. and C. Do (1996). Heat shock factor-1 mediates the transcriptional activation of Alzheimer's beta-amyloid precursor protein gene in response to stress. *Brain Res. Mol. Brain Res.* 35:325-328.
10. Engelborghs S., B. Dermaut, J. Goeman, J. Saerens, P. Marien, B. A. Pickut, B. M. Van den, S. Serneels, M. Cruts, C. van Broeckhoven, and P. P. De Deyn (2003). Prospective Belgian study of neurodegenerative and vascular dementia: APOE genotype effects. *J. Neurol. Neurosurg. Psychiatry* 74:1148-1151.
11. Engelborghs S., B. Dermaut, P. Marien, A. Symons, E. Vloeberghs, K. Maertens, N. Somers, J. Goeman, R. Rademakers, B. M. Van den, B. Pickut, M. Cruts, C. Van Broeckhoven, and P. P. De Deyn (2006). Dose-dependent effect of APOE varepsilon4 on behavioral symptoms in frontal lobe dementia. *Neurobiol. Aging* 27:285-292.

12. Fidani L., K. Rooke, M. C. Chartier-Harlin, D. Hughes, R. Tanzi, M. Mullan, P. Roques, M. Rossor, J. Hardy, and A. Goate (1992). Screening for mutations in the open reading frame and promoter of the beta-amyloid precursor protein gene in familial Alzheimer's disease: identification of a further family with APP717 Val-->Ile. *Hum. Mol. Genet.* 1:165-168.

13. Frazer K. A., L. Pachter, A. Poliakov, E. M. Rubin, and I. Dubchak (2004). VISTA: computational tools for comparative genomics. *Nucl. Acids Res.* 32:W273-W279.

14. Gentleman S. M., M. J. Nash, C. J. Sweeting, D. I. Graham, and G. W. Roberts (1993). Beta-amyloid precursor protein (beta APP) as a marker for axonal injury after head injury. *Neurosci. Lett.* 160:139-144.

15. Goate A., M.-C. Chartier-Harlin, M. Mullan, J. Brown, F. Crawford, L. Fidani, L. Giuffra, A. Haynes, N. Irving, L. James, R. Mant, P. Newton, K. Rooke, P. Roques, C. Talbot, M. Pericak-Vance, A. Roses, R. Williamson, M. Rossor, M. Owen, and J. Hardy (1991). Segregation of a missense mutation in the amyloid precursor protein gene with familial Alzheimer's disease. *Nature* 349:704-706.

16. Grilli M., M. Ribola, A. Alberici, A. Valerio, M. Memo, and P. Spano (1995). Identification and characterization of a kappa B/Rel binding site in the regulatory region of the amyloid precursor protein gene. *J. Biol. Chem.* 270:26774-26777.

17. Hofman A., W. Schulte, T. A. Tanja, C. M. van Duijn, R. Haaxma, A. J. Lameris, V. M. Otten, and R. J. Saan (1989). History of dementia and Parkinson's disease in 1st-degree relatives of patients with Alzheimer's disease. *Neurology* 39:1589-1592.

18. Iwatsubo T., A. Odaka, N. Suzuki, H. Mizusawa, N. Nukina, and Y. Ihara (1994). Visualization of A beta 42(43) and A beta 40 in senile plaques with end-specific A beta monoclonals: evidence that an initially deposited species is A beta 42(43). *Neuron* 13:45-53.

19. Izumi R., T. Yamada, S. Yoshikai, H. Sasaki, M. Hattori, and Y. Sakaki (1992). Positive and negative regulatory elements for the expression of the Alzheimer's disease amyloid precursor-encoding gene in mouse. *Gene* 112:189-195.

20. Kehoe P., V. F. Wavrant-De, R. Crook, W. S. Wu, P. Holmans, I. Fenton, G. Spurlock, N. Norton, H. Williams, N. Williams, S. Lovestone, J. Perez-Tur, M. Hutton, M. C. Chartier-Harlin, S. Shears, K. Roehl, J. Booth, W. Van Voorst, D. Ramic, J. Williams, A. Goate, J. Hardy, and M. J. Owen (1999). A full genome scan for late onset Alzheimer's disease. *Hum. Mol. Genet.* 8:237-245.

21. La Fauci G., D. K. Lahiri, S. R. J. Salton, and N. K. Robakis (1989). Characterization of the 5'-end region and the first two exons of the b-protein precursor gene. *Biochem. Biophys. Res. Commun.* 159:297-304.

22. Lahiri D. K. and C. Nall (1995). Promoter activity of the gene encoding the beta-amyloid precursor protein is up-regulated by growth factors, phorbol ester, retinoic acid and interleukin-1. *Brain Res. Mol. Brain Res.* 32:233-240.

23. Lahiri D. K. (2004). Functional characterization of amyloid b precursor protein regulatory elements. Rationale for the identification of genetic polymorphism. *Ann. N.Y. Acad. Sci.* 1030:282-288.

24. Lahiri D. K., C. Nall, and Y.-W. Ge (1999). Promoter activity of the beta-amyloid precursor protein gene is negatively modulated by an upstream regulatory element. *Mol. Brain Res.* 71:32-41.

25. Liddell M. B., A. J. Bayer, and M. J. Owen (1995). No evidence that common allelic variation in the Amyloid Precursor Protein (APP) gene confers susceptibility to Alzheimer's disease. *Hum. Mol. Genet.* 4:853-858.

26. McKhann G., D. Drachman, M. Folstein, R. Katzman, D. Price, and E. M. Stadlan (1984). Clinical diagnosis of Alzheimer's disease: report of the NINCDS-ADRDA Work Group under the auspices of Department of Health and Human Services Task Force on Alzheimer's Disease. *Neurology* 34:939-944.

27. Myers A., F. Wavrant De-Vrieze, P. Holmans, M. Hamshere, R. Crook, D. Compton, H. Marshall et al. (2002). Full genome screen for Alzheimer disease: stage II analysis. *Am. J. Med. Genet.* 114:235-244.

28. Olson J. M., K. A. Goddard, and D. M. Dudek (2001). The amyloid precursor protein locus and very-late-onset Alzheimer disease. *Am. J. Hum. Genet.* 69:895-899.

29. Olson J. M., K. A. Goddard, and D. M. Dudek (2002). A second locus for very-late-onset Alzheimer disease: a genome scan reveals linkage to 20p and epistasis between 20p and the amyloid precursor protein region. *Am. J. Hum. Genet.* 71:154-161.

30. Pericak-Vance M. A., J. L. Bebout, P. C. Gaskell, Jr., L. H. Yamaoka, W. Y. Hung, M. J. Alberts, A. P. Walker, R. J. Bartlett, C. A. Haynes, K. A. Welsh, N. L. Earl, A. Heyman, C. M. Clark, and A. D. Roses (1991). Linkage studies in familial Alzheimer disease: Evidence for chromosome 19 linkage. *Am. J. Hum. Genet.* 48:1034-1050.

31. Pollwein P., C. L. Masters, and K. Beyreuther (1992). The expression of the amyloid precursor protein (APP) is regulated by two GC-elements in the promoter. *Nucleic Acids Res.* 20:63-68.

32. Quandt K., K. Frech, H. Karas, E. Wingender, and T. Werner (1995). MatInd and MatInspector: new fast and versatile tools for detection of consensus matches in nucleotide sequence data. *Nucleic Acids Res.* 23:4878-4884.

33. Querfurth H. W., J. Jiang, W. Xia, and D. J. Selkoe (1999). Enhancer function and novel DNA binding protein activity in the near upstream betaAPP gene promoter. *Gene* 232:125-141.

34. Quitschke W. W., J. P. Matthews, R. J. Kraus, and A. A. Vostrov (1996). The initiator element and proximal upstream sequences affect transcriptional activity and start site selection in the amyloid beta-protein precursor promoter. *J. Biol. Chem.* 271:22231-22239.

35. Rogaev E. I., W. J. Lukiw, G. Vaula, J. L. Haines, E. A. Rogaeva, T. Tsuda, N. Alexandrova et al. (1993). Analysis of the c-fos gene on chromosome 14 and the promoter of the amyloid precursor protein gene in familial Alzheimer's disease. *Neurology* 43:2275-2279.

36. Rooke K., A. Goate, L. Fidani, M. Mullan, P. Roques, M. Rossor, J. Hardy, and M. C. Chartier-Harlin (1992). Screening of the promoter and the b-amyloid sequence of the APP gene for polymorphisms in families with late onset Alzheimer's disease. *Neurodegen.* 1:237-240.

37. Rumble B., R. Retallack, C. Hilbich, G. Simms, G. Multhaup, R. Martins, A. Hockey, P. Montgomery, K. Beyreuther, and C. L. Masters (1989). Amyloid A4 protein and its precursor in Down's syndrome and Alzheimer's disease. *N. Engl. J. Med.* 320:1446-1452.

38. Salbaum J. M., A. Weideman, H.-G. Lemaire, C. L. Masters, and K. Beyreuther (1988). The promoter of Alzheimer's disease amyloid A4 precursor gene. *EMBO J.* 7:2807-2813.
39. Scheuner D., C. Eckman, M. Jensen, X. Song, M. Citron, N. Suzuki, T. D. Bird, J. Hardy, M. Hutton, W. Kukull, E. Larson, E. Levy-Lahad, M. Viitanen, E. Peskind, P. Poorkaj, G. Schellenberg, R. Tanzi, W. Wasco, L. Lannfelt, D. Selkoe, and S. Younkin (1996). Secreted amyloid b-protein similar to that in the senile plaques of Alzheimer's disease is increased in vivo by the presenilin 1 and 2 and APP mutations linked to familial Alzheimer's disease. *Nat. Med.* 2:864-870.
40. Siman R., J. P. Card, R. B. Nelson, and L. G. Davis (1989). Expression of beta-amyloid precursor protein in reactive astrocytes following neuronal damage. *Neuron* 3:275-285.
41. Sola C., F. J. Garcia-Ladona, G. Mengod, A. Probst, P. Frey, and J. M. Palacios (1993). Increased levels of the Kunitz protease inhibitor-containing beta APP mRNAs in rat brain following neurotoxic damage. *Brain Res. Mol. Brain Res.* 17:41-52.
42. Song W. and D. K. Lahiri (1998). Functional identification of the promoter of the gene encoding the Rhesus monkey beta-amyloid precursor protein. *Gene* 217:165-176.
43. Suzuki N., T. T. Cheung, X.-D. Cai, A. Odaka, L. Otvos Jr., C. Eckman, T. E. Golde, and S. G. Younkin (1994). An increased percentage of long amyloid b protein secreted by familial amyloid b protein precursor (bAPP717) mutants. *Science* 264:1336-1340.
44. Theuns J. and C. Van Broeckhoven (2000). Transcriptional regulation of Alzheimer's disease genes: implications for susceptibility. *Hum. Mol. Genet.* 9:2383-2394.
45. Vandesompele J., K. De Preter, F. Pattyn, B. Poppe, N. Van Roy, A. De Paepe, and F. Speleman (2002). Accurate normalization of real-time quantitative RT-PCR data by geometric averaging of multiple internal control genes. *Genome Biol.* 3:RESEARCH0034.
46. Wavrant-De Vrieze F., R. Crook, P. Holmans, P. Kehoe, M. J. Owen, J. Williams, K. Roehl, D. K. Laliiri, S. Shears, J. Booth, W. Wu, A. Goate, M. C. Chartier-Harlin, J. Hardy, and J. Perez-Tur (1999). Genetic variability at the amyloid-beta precursor protein locus may contribute to the risk of late-onset Alzheimer's disease. *Neurosci. Lett.* 269:67-70.
47. Weckx S., J. Del Favero, R. Rademakers, L. Claes, M. Cruts, P. De Jonghe, C. Van Broeckhoven, and P. De Rijk (2005). novoSNP, a novel computational tool for sequence variation discovery. *Genome Res.* 15:436-442.
48. Wirak D. O., R. Bayney, C. A. Kundel, A. Lee, G. A. Scangos, B. D. Trapp, and A. J. Unterbeck (1991). Regulatory region of human amyloid precursor protein (APP) gene promotes neuron-specific gene expression in the CNS of transgenic mice. *EMBO J.* 10:289-296.
49. Wisniewski K. E., A. J. Dalton, D. R. Crapper-McLachlan, G. Y. Wen, and H. M. Wisniewski (1985). Alzheimer's disease in Down's syndrome: Clinicopathologic studies. *Neurology* 35:957-961.
50. Yamada T., H. Sasaki, K. Dohura, I. Goto, and Y. Sakaki (1989). Structure and expression of the alternatively-spliced forms of mRNA for the mouse homolog of Alzheimer's disease amyloid beta protein precursor. *Biochem. Biophys. Res. Commun.* 158:906-912.
51. Yoshikai S., H. Sasaki, K. Doh-ura, H. Furuya, and Y. Sakaki (1990). Genomic organization of the human amyloid beta-protein precursor gene. *Gene* 87:257-263.

The invention claimed is:

1. A method of determining increased risk for developing Alzheimer's disease in a subject, the method comprising:
determining if a sample isolated from the subject comprises a mutation in a nucleotide sequence comprising an amyloid precursor protein regulatory region relative to a wild type nucleotide sequence comprising an amyloid precursor protein regulatory region wherein the mutation is selected from the group consisting of −118C>A, −369C>G, and −534G>A of SEQ ID NO:1;
wherein said mutation in said nucleotide sequence results in at least a 1.2 times increase in amyloid precursor protein expression compared to wild type expression; and
wherein said mutation in the nucleotide sequence increases the risk of the subject developing Alzheimer's disease.

2. A method of diagnosing Alzheimer's disease in a subject, the method comprising:
determining if a sample isolated from the subject comprises a mutation in a nucleotide sequence comprising an amyloid precursor protein regulatory region relative to a wild type nucleotide sequence comprising an amyloid precursor protein regulatory region wherein the mutation is selected from the group consisting of −118C>A, −369C>G, −479C>T, and −534G>A, of SEQ ID NO:1;
wherein said regulatory region is the proximal promoter region, and
wherein the mutation is in the nucleotide sequence is indicative for the presence of Alzheimer's disease in the subject.

3. A method of determining increased risk for developing Alzheimer's disease in a subject, the method comprising:
determining if a sample isolated from the subject comprises a mutation in a nucleotide sequence comprising an amyloid precursor protein regulatory region relative to a wild type nucleotide sequence comprising an amyloid precursor protein regulatory region wherein said mutation is selected from the group consisting of −118C>A, −369C>G, −479C>T, and −534G>A of SEQ ID NO:1;
wherein said regulatory region is the proximal promoter region; and
wherein said mutation in the nucleotide sequence increases the risk of the subject developing Alzheimer's disease.

4. The method of claim 3, wherein the mutation is −118C>A of SEQ ID NO:1.

5. The method of claim 3, wherein the mutation is −369C>G of SEQ ID NO:1.

6. The method of claim 3, wherein the mutation is −479C>T of SEQ ID NO:1.

7. The method of claim 3, wherein the mutation is −534G>A of SEQ ID NO:1.

* * * * *

```
SEQUENCE LISTING

<160> NUMBER OF SEQ ID NOS: 47

<210> SEQ ID NO 1
<211> LENGTH: 9500
<212> TYPE: DNA
<213> ORGANISM: Homo sapiens
<220> FEATURE:
<221> NAME/KEY: misc_feature
<222> LOCATION: (8467)..(8467)
<223> OTHER INFORMATION: n (corresponding to relative position -534) can
      be G or A
<220> FEATURE:
<221> NAME/KEY: misc_feature
<222> LOCATION: (8522)..(8522)
<223> OTHER INFORMATION: n (corresponding to relative position -479) can
      be C or T
<220> FEATURE:
<221> NAME/KEY: misc_feature
<222> LOCATION: (8632)..(8632)
<223> OTHER INFORMATION: n (corresponding to relative position -369) can
      be C or G
<220> FEATURE:
<221> NAME/KEY: misc_feature
<222> LOCATION: (8883)..(8883)
<223> OTHER INFORMATION: n (corresponding to relative position -118) can
      be C or A
<220> FEATURE:
<221> NAME/KEY: misc_feature
<222> LOCATION: (9000)..(9000)
<223> OTHER INFORMATION: corresponding to relative position -1
<220> FEATURE:
<221> NAME/KEY: misc_feature
<222> LOCATION: (9001)..(9001)
<223> OTHER INFORMATION: corresponding to relative position +1 (Start
      Transcription)
```

<400> SEQUENCE: 1

```
gatcatgatt ggtaaatctg tagtgactaa ttgcccactg ctgcctattc catctgacct      60
aaattcctca ggtcttctaa cattaagacc tcttcctggc cggttgtgct ggctcatgcc     120
tgtaattcca cactttaggc agctgaggca aggcagatca cttgaggtca agagttcaag     180
accagcctgg ccaacatggt gaagcccgtg tctgtactaaa aaatacaaaa attagccgga    240
cctggtggtg cgtgcctgta atcccagcta ctcgggaggc tgagtcagga gaatcacttg    300
aacccgggc agcgggggag gctgcagtga gtggagatca aaccaccgca ctccagccca     360
ggtgacagag caagagtcag tctcaaaaaa aaaaaaacaa aaaaaaaac ctcttcctat     420
agctaactcc cacttaccac ccccatcatg aacactcttg atgtatttac atggtttctc    480
cttcgaacat cctcctttct tctttcttaa tggttgttat caaatacct gataaaaaac     540
aaaaacaaaa aacctcctct gaaggtccct tattcaccct tccaacgcta caggtctgta    600
actctcattt tctttttaaa aaattttat ttttttaatt tattttattt ttttttcag      660
acggagtctt gctctgtcgc ccaggctgga gtgcagtgac acgatctcgg ctcactgcaa    720
cctccacttc ccaggttcaa gcaattctcc tgcctcagcc tcctgagttg ctgggattac    780
aggtgcctac caccacacct gacctcaagt aacccaccca cctcgacctc ccaaagtgct    840
gagaatacag gtgtgagcca tcatgcctgg ccaaaatttt taaattttaa aaatatatt    900
ttattttttg tagagacagg gtctcatttt gagcccaaac tggtcttgaa ctcctaggct    960
caagtgatcc tcctgccttg gcctcccaaa atgctgggat tataggcaca agccaccagg   1020
cctgatcctt acttttcttc tgatgaattc acatatatgt gcacaaatac tttatactaa   1080
attgtattta ctgatgtact ttttcactg tgccttttct ttttcttgcc cagatatttt    1140
tctcatataa acattagctc cttaatggga gcaaatgaac cagtttttt ttaattccca    1200
cccaaagtga gaatataaaa attttttatt gatccaccaa tactgaacac tttcatttct   1260
aatagttata tttaactgaa taaattacac acgggacaaa aatgttattt aagggataaa   1320
gttgggtgtt tgctcaggga caacgttgta tattgaatga tttggtgctt ttgtgaattt   1380
atcattcaaa agaccatcgt gatggctaaa taacagaaag gagagcttta ttggcaatat   1440
caatttgcaa acccggaaga catagtcttc ggtgtatgct gaatgtggtc tctcttcaaa   1500
agagaggaag gacagttggg tttcatgcct cacagggtct gtttcacaca gtggagtcat   1560
acatattcag caggttttgga ggaaaagata tacatattta tgaggggagc tgagtgcatg   1620
tgcaatgggt aaatatgtat gtgacatccc atgtacactt tggggcaggg ttttagtgtt   1680
aaaatgaggt aaaatttggc tctttacatc aaaaggtgaa ctacaggacc caaagacagt   1740
ttgtgcacag cctctaataa actggctgac actggcttaa ggtctgcaat tgcttatcag   1800
aaaagaatgt ttgtaaggct ggtcctcatt ccaattagag ttgtagtggt ctgggttgta   1860
aatcacagga tggggctgat agttcctatt attagggagt ttagagccat agaaattgag   1920
aaattggtca tgccagccag tccccgaacc ctaaccctgt aggtaacttt gtttccttaa   1980
ccttacagtc catcttaggt gataaagggg tgtctgtttt ggtatctcac atcacaaatt   2040
gttggttggt ttgtgtgttt gtttcatcat tcaggatgtt gtttctttag ggaatgtgaa   2100
cctgaattct caaggcttgt tagactgtaa tgttcccatt cattttaggt ttagctcatg   2160
cttctctagc cacagccttc acttggattt taaagttga attactcatc aaagtctcta   2220
ggacacgaaa gacaatcctt aggtatgatt tgaccagtaa aaaagagatc cagctgcctt   2280
gaagcataag atcccctcgg ctccaatgtc tatcactaat attcagtgtg caaggatcc    2340
```

```
caggccacag agctgtggct tcctgcagct gctctgggga gtgactctct tggagcatgt    2400
gatgtggtct tccattgtgc aggaccagcc cagtggcatc ctttcaacac ctctggcaag    2460 cagccttttcc aagcacgggt gccgtctgaa aacaggaggc atatctttca catcctaggc    2520
acacgcccta gggagtggtc agggttttgt ccagttctca gcaaactagc tacagctcca    2580
tcccttactc ccacactcaa gagagatact agaatacaac tgagagtagc ctgatatgat    2640
gctaacctcg agttgctttt atttaaatta aaataaatca accagacaca gtggctcatg    2700
cctataatcc ctgcatttta ggagatcaag gagggtggat cacgagctca ggagtttaag    2760
accaacctgg ataacatggc aagaccccat ctctacaaaa agtacacaaa ttagctggac    2820
atggtagtgc gcacctgtag ccccagctac tctggaggct gaggtgaagg atcacttgag    2880
cccaggaggt agaggttgca gtgagctgag attgtgccac tgctaataat taattaaata    2940
attaattaaa ttaataaatc gtgccacttt attaaataaa taaaacaaga gtaaatcact    3000
cacaaatttg gagcttttat tagcaaaaca ttacttagga aatctaaata aataacacgg    3060
ggttgacagc cattgttcta actggcagcc cctggcaagc tcaaagccag gattatgctg    3120
gtcacttaag tgacagctat tgcgaattgt tgttctctca agaaaaaaga accgatttct    3180
atggtaaacc aggcactgtg ctgggtgcct ttacaattca tcaccacacc acctaatgaa    3240
aggagcattc ttcagaaact gtagtgctca ggctttctca aggcctgagt tcttttccac    3300
cagagcatat tgttgcccta ttatccaaag ttctctaagg aagagaactg acgtaagacc    3360
cacatggctc cattacatct tctggctact tgattgattt tcatactccc tacctctggg    3420
gttggtatgt actatctatt tctttctcct ctcgttcttc ctttttattc cataaaatac    3480
aggaatattc ctgtacatta gtccttgcag caaccttgga attactacat tcctcaaaca    3540
agttatggaa gccagctgcc aatattggtc cctggttaaa cagtgaattc tgttgttcca    3600
tagagttact actgaaatac ctaagccatt ttgtaaaata taatttagtt gatctgaagg    3660
ctgtctctaa agcagtttta tgtagtgatt acagagaagg actaatttca agagtatttt    3720
attgtttaaa aaaatgtaaa cattttatgg atgcactagt gaagtaaaga ccaataaatg    3780
aagcagtaac tttaataaaa gggtaagtaa aatgtcacat cctctgccta tattcaggtc    3840
tgttaggtat gtgtagttaa atgtaggtaa gttagttgat aattatttat ttaagcatttt    3900 ctttatgtct actcattaaa aagaaaaaaa gattaaaaga atgttactat gtgaaaaact    3960
gcccatcact ggggaaaaga atttatttat gcaaagcttc aacgctattt acagtttaga    4020
cttttgtagc tattgaaggc tgacattgag ataaagaagt taatcatgtc cttctgtctt    4080
ggaggaggta gaaagagatg agaatgaata caattcagga tctacttctg gtctttgatg    4140
aggagttagc acacggttct gggaggaaag acaggttaag aggcatgtga aactctcaaa    4200
tacgtcactg cgtctgccaa cgtacatgat acccagcaag ctcacatctt catggaaagc    4260
atggtaattc ccaacactac cggaagtctg gagtggctaa gtaatccata tattcaacca    4320
ggaagcagct aaagaaatat tctaattacc taggaaggtt tctgatttca aaggacatg     4380 aataaaaagt agaaggaatc cactcccaag gacggacatc agagtagctt aaaatgtgag    4440
aataatttta ggggaatttt agaggtttgg ttatagactt atgttccccc aaaattcata    4500
tgttgaagcc ctaaccccca gtaccttaga acatgactgt atttgggtag ggcctttgaa    4560
gagctaatta aattaaggcc actggcgtgg gccctaatat aatctggctg gtattcttgt    4620
aagaggagga gattaggaca cacagaaata ccagaggtac ctgtgcagag gaaagaacgt    4680
gtgaggactt agcaagggtg cagccatctg caagccaagg agacctctga ggattccaat    4740
```

```
cctatctgca tcttgatctt agacttttct ggaactgtga gaaaataaat ttcttggttt    4800
aagccaccca gtctgtgata ttttgttatg gcagctctag taaactaata cagattttaa    4860
atgtcattaa atgtcaatgt ttaagctttg acaaaatttt ctaaaggaaa gtataaaagg    4920
tcattttctt tcttttcaga gcctgatgat tgcgggaggg gtaagccagc tgcatgggga    4980
tcatgatgca atgctgatgc aggacagaca gaaagtagat ctcttccatt tctatttttt    5040 tttttctgt tgagttgaat gatcttcaga ctgaaaatga agaaaggtc actggaaata    5100 aaggccaaag atgagtgaca ggattataga ataagtctta gctgttctaa agaaggacat    5160
attatgtacc cccaccccca aattcatatg ttgaagtcct aacccgacag tgtctcaaaa    5220
tgtgaccata tttggagata gggtcaaaga tgtaattaag gttaaatgag gtcattagca    5280
tggatcctaa cccaatatct gctgtcctta taacaagagg agattagggc acagtaagac    5340
acagagggaa gaccatgtga gaatacaggg agaaggtggc catctgcaag ccaaggagag    5400
aggcctcaga agtaaccaac tcagccaaca cctcgatttc agacttccag cctcctgaaa    5460
tgtgaggaaa tacatttctg gtgtttgatc catccagtct atggtaagtt atggcacccc    5520
tgcagggttc atctggctca gacttaacga ttgcttttgg tgatatttat agggcacaga    5580
taacagccta aacacaagac gacagaaacg cggcccagca gactatgcat aaaatagaaa    5640
tggggtatct ggaccaattg gagtctgcag tgggatgcgg ttactaaaac agtcaaatgc    5700
aacatgaggc tccaggcaga gtagtgggca acatctccca tgttgcagca gtcagagcac    5760
acttcgagta ctgtaaaaag acacagacaa gccagaacac atttagagaa tggccaaggt    5820
gtggaaggaa ccagaaacca tgccattatg caactgttga aggaagtgcc tgttttacct    5880
tgtgaagaga agactctaga ggaagaagta gcatgaaaac cgctggcaaa tttgtaaaga    5940
tctgaagtgt ggaaaagaat tattctgctt ggtcactggg gatacaagga tatctgagtg    6000
ggagtttaaa ggcggggat gtgagcttta aatgggataa gaacattcta gtaaccagaa    6060
atgcccaaag atagaatgca cagtctggag agccagtgaa tatctcacaa atggagacac    6120
ttgaaactag gatggggatg ctgttgtagg aattccagca gacaagtggt tgttggttcc    6180
ttccccaact ttgtagggtt ataactaggg atgttcctgc gttttctgct tggaggatct    6240
gcaagacacc tcagggcagg aaatggcatt aaatgcagaa cagagctagt ggctgaaaag    6300
caaaaagcca tcaggatctc tgagtagtga aggaaccaga gaacatgcag gcaatgtcca    6360
tcattctgac gcaatcagca gcataatcat cttcccccag gaacatcttg accagggaat    6420
gtgtcagtgt ggtgaatttc aacagtggaa agagaaactg ctaaatctaa gaactttaat    6480
ttttatagat tatgatctca tctctacaat tttgaatttc atgctcaata aaagttcctt    6540
actctctttt ttttttttg agacggagtc tcgctctgtc gcccaggctg gagtgcagtg    6600
gcgcgatctc ggctcacttc aagctcagcc tcccgggttc acgccattct cctgcctcag    6660 cctcccagt agctgggact acaggcgccc gccacgacgc ccggctaatt ttttgtattt    6720
ttagtagaga cggggtttca ccgtgttagc caggatggtg ttgatctcct gacctcgtga    6780
tccgcccgcc tcagcctccc aaagaaaagt ccctcactct taaagttgcc tcctccttcc    6840
cagggctggc ttcatgggca tgcaaccctg gagagtctca caggccctgc ggtgggagga    6900
gccccatgct tggtttaacg ctctgccatt gccatcttaa aattcttaat ttaattttt    6960 ttctttttt tgaggtggag tctcgctctg tcgcccaggc tggagtgcaa tggcacaatc    7020
ttggctcact gcaacctccg cctcccaggt tcaagcgatt ctcctgcctc agcctctgga    7080
gtagctggga ttacaggcag gagtaaccac gctcggctaa tttttgcatt tttagtagag    7140
```

```
atggggggttt caccatgttg gccaggctgg tctagaactc ctgacctcag gtgatctgcc   7200
cacctgggcc tcctaaagtg ctgggattac aggcatgagc caccaggccc ggccttaaaa   7260
ttcttaataa tgtaacaaag ggtctcacgt ttgcattttg cagtggactc tgcaagattt   7320
gtagctttgg accacgtttc tctttgcatt cagataccct cttttttgcc ttatttgctc   7380
atgcagaccc ggaacaaata cggaattgcg gtgggtaaat gtggtgcaga aagtgaacaa   7440
ctgggtttgt cctgtcactt taggcttttc cctgctgtcc cagcttcatg tcacttactt   7500
gctattagat ttgggagttc attagcttca ttttcctgat gtataaatag gaataatagt   7560
aacagcctct ttggcttttg taggaagtaa atgcatgaa gcgtataaac aaatactgca   7620
tgacaataaa tatttgtcct tatttgttga ggacatccaa aggacattca ggggcaaaag   7680
taatccaaga gtcaagactg aatgcctagt gcgggaaaag acacacaaga caacatttag   7740
gggagctggt acagaaatga cttcccagga aggaagtctg taccccgctg gctgagccat   7800
ccttcccggg cctaggcacc cttgtcagcg caatgagcaa gggagagaag gcaggctgca   7860
gtgcagccct cagaagggcc agagcactcc ctggcttcag tccttcgctc caagccctgt   7920
gtggagtggg ctgtggcttg gtaactaaat gctacttcag gtcaagagca ggggatatat   7980
ctgggcagtt ctagagcatt ctaaactatc tggacactaa ctggacagtg gacggtttgt   8040
gtttaatcca ggagaaagtg gcatggcaga aggttcattt ctataattca ggacagacac   8100
aatgaagaac aagggcagcg tttgaggtca gaagtcctca tttacggggg tcgaatacga   8160
atgatctctc ctaattttc cttcttcccc aactcagatg gatgttacat ccctgcttaa   8220
caacaaaaaa agaccccccg ccccgcaaaa tccacactga ccacccccett taacaaaaca   8280
aaaccaaaaa caaacaaaaa tataagaaag aaacaaaacc caagcccaga accctgcttt   8340
caagaagaag taaatgggtt ggccgcttct ttgccaggtc ctgcgccttg ctcctttggt   8400
tcgttctaaa gatagaaatt ccaggttgct cgtgcctgct tttgacgttg ggggttaaaa   8460
aatgagnttt tgctgtctca acaagcaaag aaaatcctat ttcctttaag cttcactcgt   8520
tntcattctc ttccagaaac gcctgcccca cctctccaaa ccgagagaaa aaacgaaatg   8580
cggataaaaa cgcaccctag cagcagtcct ttatacgaca ccccccgggag gnctgcgggg   8640
tcggatgatt caagctcacg gggacgagca ggagcgctct cgactttct agagcctcag   8700
cgtcctagga ctcaccttc cctgatcctg caccgtccct ctcctggccc cagactctcc   8760
ctcccactgt tcacgaagcc caggtgggcc gtcggccggg gagcggaggg ggcgcgtggg   8820
gtgcaggcgg cgccaagggc gcgtgcacct gtgggcgcgg ggcgcgaggg cccctcccgg   8880
cgngagcggg cgcagttccc cggcggcgcc gctaggggtc tctctcgggt gccgagcggg   8940
gtgggccgga tcagctgact cgcctggctc tgagccccgc cgccgcgctc gggctccgtc   9000
agtttcctcg gcagcggtag gcgagagcac gcggaggagc gtgcgcgggg gccccgggag   9060
acggcggcgg tggcggcgcg ggcagagcaa ggacgcggcg gatcccactc gcacagcagc   9120
gcactcggtg ccccgcgcag ggtcgcgatg ctgcccggtt tggcactgct cctgctggcc   9180
gcctggacgg ctcgggcgct ggaggtgggt gccgcgcctc ggaaggcggg gggaggctgc   9240
acggtgggga cgcgataccc cccaagacct taacccaagt ctttaatgca gagaagccgg   9300
gggtccgtca atgggacccc tctcctctcc gccccgcctt cgcgacgtcc agcgcatccc   9360
cgcttcggc ccagccctgc cccagggagt cgcgctccgg cccgctgaga gggagcgggc   9420
gaggcgctgg tctccctggt tccgcgccag cccggggcga aagggtaggg gggcgaccct   9480
gagcccagac ccgacttag                                               9500
```

<210> SEQ ID NO 2
<211> LENGTH: 18
<212> TYPE: DNA
<213> ORGANISM: Artificial Sequence
<220> FEATURE:
<223> OTHER INFORMATION: Chemically Synthesized - Primer

<400> SEQUENCE: 2
cccccgcccc gcaaaatc                                             18

<210> SEQ ID NO 3
<211> LENGTH: 28
<212> TYPE: DNA
<213> ORGANISM: Artificial Sequence
<220> FEATURE:
<223> OTHER INFORMATION: Chemically Synthesized - Primer

<400> SEQUENCE: 3
tgggcttcgt gaacagtggg agggagag                                  28

<210> SEQ ID NO 4
<211> LENGTH: 24
<212> TYPE: DNA
<213> ORGANISM: Artificial Sequence
<220> FEATURE:
<223> OTHER INFORMATION: Chemically Synthesized - Primer

<400> SEQUENCE: 4
atgattcaag ctcacgggga cgag                                      24

<210> SEQ ID NO 5
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 5
gctcagagcc aggcgagtca gc                                        22

<210> SEQ ID NO 6
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 6
ggcggcgccg ctagggtct ct                                         22

<210> SEQ ID NO 7
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 7
ctccagcgcc cgagccgtcc ag                                        22

<210> SEQ ID NO 8
<211> LENGTH: 22
<212> TYPE: DNA
<213> ORGANISM: Artificial Sequence
<220> FEATURE:
<223> OTHER INFORMATION: Chemically Synthesized - Primer

```
<400> SEQUENCE: 8
gacgcaatca gcagcataat ca                                              22

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 9
ctgggaagga ggaggcaact                                                 20

<210> SEQ ID NO 10
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 10
catgcttggt ttaacgctct gc                                              22

<210> SEQ ID NO 11
<211> LENGTH: 25
<212> TYPE: DNA
<213> ORGANISM: Artificial Sequence
<220> FEATURE:
<223> OTHER INFORMATION: Chemically Synthesized - Primer

<400> SEQUENCE: 11
gttcactttc tgcaccacat ttacc                                           25

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 12
gacgcaatca gcagcataat ca                                              22

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 13
gatctcggct cacttcaagc                                                 20

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 14
ctgggaagga ggaggcaact                                                 20

<210> SEQ ID NO 15
<211> LENGTH: 18
```

```
<212> TYPE: DNA
<213> ORGANISM: Artificial Sequence
<220> FEATURE:
<223> OTHER INFORMATION: Chemically Synthesized - Primer

<400> SEQUENCE: 15
aaattagccg ggcgtcgt                                                    18

<210> SEQ ID NO 16
<211> LENGTH: 14
<212> TYPE: DNA
<213> ORGANISM: Artificial Sequence
<220> FEATURE:
<223> OTHER INFORMATION: Chemically Synthesized - Primer

<400> SEQUENCE: 16
gtagtcccag ctac                                                        14

<210> SEQ ID NO 17
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 17
catgcttggt ttaacgctct gc                                               22

<210> SEQ ID NO 18
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 18
attctcctgc ctcagcctct                                                  20

<210> SEQ ID NO 19
<211> LENGTH: 25
<212> TYPE: DNA
<213> ORGANISM: Artificial Sequence
<220> FEATURE:
<223> OTHER INFORMATION: Chemically Synthesized - Primer

<400> SEQUENCE: 19
gttcactttc tgcaccacat ttacc                                            25

<210> SEQ ID NO 20
<211> LENGTH: 26
<212> TYPE: DNA
<213> ORGANISM: Artificial Sequence
<220> FEATURE:
<223> OTHER INFORMATION: Chemically Synthesized - Primer

<400> SEQUENCE: 20
gtgaaacccc catctctact aaaaat                                           26

<210> SEQ ID NO 21
<211> LENGTH: 16
<212> TYPE: DNA
<213> ORGANISM: Artificial Sequence
<220> FEATURE:
<223> OTHER INFORMATION: Chemically Synthesized - Primer

<400> SEQUENCE: 21
gctgggatta caggca                                                      16
```

<210> SEQ ID NO 22
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 22
catgcttggt ttaacgctct gc                                          22

<210> SEQ ID NO 23
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 23
cctgacctca ggtgatctgc                                             20

<210> SEQ ID NO 24
<211> LENGTH: 25
<212> TYPE: DNA
<213> ORGANISM: Artificial Sequence
<220> FEATURE:
<223> OTHER INFORMATION: Chemically Synthesized - Primer

<400> SEQUENCE: 24
gttcactttc tgcaccacat ttacc                                       25

<210> SEQ ID NO 25
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 25
gcaaacgtga gacccttttgt                                            20

<210> SEQ ID NO 26
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 26
attattaaga attttaaggc                                             20

<210> SEQ ID NO 27
<211> LENGTH: 20
<212> TYPE: DNA
<213> ORGANISM: Artificial Sequence
<220> FEATURE:
<223> OTHER INFORMATION: Chemically Synthesized - Primer

<400> SEQUENCE: 27
gaaattccag gttgctcgtg                                             20

<210> SEQ ID NO 28
<211> LENGTH: 20
<212> TYPE: DNA
<213> ORGANISM: Artificial Sequence
<220> FEATURE:
<223> OTHER INFORMATION: Chemically Synthesized - Primer

```
<210> SEQ ID NO 28
<400> SEQUENCE: 28
ggcgtttctg gaagagaatg                                             20

<210> SEQ ID NO 29
<211> LENGTH: 17
<212> TYPE: DNA
<213> ORGANISM: Artificial Sequence
<220> FEATURE:
<223> OTHER INFORMATION: Chemically Synthesized - Primer

<400> SEQUENCE: 29
gggggttaaa aaatgag                                                17

<210> SEQ ID NO 30
<211> LENGTH: 26
<212> TYPE: DNA
<213> ORGANISM: Artificial Sequence
<220> FEATURE:
<223> OTHER INFORMATION: Chemically Synthesized - Primer

<400> SEQUENCE: 30
ctgtctcaac aagcaaagaa aatcct                                      26

<210> SEQ ID NO 31
<211> LENGTH: 18
<212> TYPE: DNA
<213> ORGANISM: Artificial Sequence
<220> FEATURE:
<223> OTHER INFORMATION: Chemically Synthesized - Primer

<400> SEQUENCE: 31
gtggggcagg cgtttctg                                               18

<210> SEQ ID NO 32
<211> LENGTH: 16
<212> TYPE: DNA
<213> ORGANISM: Artificial Sequence
<220> FEATURE:
<223> OTHER INFORMATION: Chemically Synthesized - Primer

<400> SEQUENCE: 32
ttaagcttca ctcgtt                                                 16

<210> SEQ ID NO 33
<211> LENGTH: 18
<212> TYPE: DNA
<213> ORGANISM: Artificial Sequence
<220> FEATURE:
<223> OTHER INFORMATION: Chemically Synthesized - Primer

<400> SEQUENCE: 33
cccccgcccc gcaaaatc                                               18

<210> SEQ ID NO 34
<211> LENGTH: 18
<212> TYPE: DNA
<213> ORGANISM: Artificial Sequence
<220> FEATURE:
<223> OTHER INFORMATION: Chemically Synthesized - Primer

<400> SEQUENCE: 34
cccccgcccc gcaaaatc                                               18

<210> SEQ ID NO 35
<211> LENGTH: 28
```

```
<212> TYPE: DNA
<213> ORGANISM: Artificial Sequence
<220> FEATURE:
<223> OTHER INFORMATION: Chemically Synthesized - Primer

<400> SEQUENCE: 35
tgggcttcgt gaacagtggg agggagag                                          28

<210> SEQ ID NO 36
<211> LENGTH: 28
<212> TYPE: DNA
<213> ORGANISM: Artificial Sequence
<220> FEATURE:
<223> OTHER INFORMATION: Chemically Synthesized - Primer

<400> SEQUENCE: 36
tgggcttcgt gaacagtggg agggagag                                          28

<210> SEQ ID NO 37
<211> LENGTH: 24
<212> TYPE: DNA
<213> ORGANISM: Artificial Sequence
<220> FEATURE:
<223> OTHER INFORMATION: Chemically Synthesized - Primer

<400> SEQUENCE: 37
atgattcaag ctcacgggga cgag                                              24

<210> SEQ ID NO 38
<211> LENGTH: 15
<212> TYPE: DNA
<213> ORGANISM: Artificial Sequence
<220> FEATURE:
<223> OTHER INFORMATION: Chemically Synthesized - Primer

<400> SEQUENCE: 38
agggcgctgc acctg                                                        15

<210> SEQ ID NO 39
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 39
gctcagagcc aggcgagtca gc                                                22

<210> SEQ ID NO 40
<211> LENGTH: 16
<212> TYPE: DNA
<213> ORGANISM: Artificial Sequence
<220> FEATURE:
<223> OTHER INFORMATION: Chemically Synthesized - Primer

<400> SEQUENCE: 40
ctcggcaccc gagaga                                                       16

<210> SEQ ID NO 41
<211> LENGTH: 14
<212> TYPE: DNA
<213> ORGANISM: Artificial Sequence
<220> FEATURE:
<223> OTHER INFORMATION: Chemically Synthesized - Primer

<400> SEQUENCE: 41
gaactgcgcc cgct                                                         14
```

```
<210> SEQ ID NO 42
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 42
ggcggcgccg ctagggtct ct                                               22

<210> SEQ ID NO 43
<211> LENGTH: 18
<212> TYPE: DNA
<213> ORGANISM: Artificial Sequence
<220> FEATURE:
<223> OTHER INFORMATION: Chemically Synthesized - Primer

<400> SEQUENCE: 43
gggctccgtc agtttcct                                                   18

<210> SEQ ID NO 44
<211> LENGTH: 22
<212> TYPE: DNA
<213> ORGANISM: Artificial Sequence
<220> FEATURE:
<223> OTHER INFORMATION: Chemically Synthesized - Primer

<400> SEQUENCE: 44
ctccagcgcc cgagccgtcc ag                                              22

<210> SEQ ID NO 45
<211> LENGTH: 16
<212> TYPE: DNA
<213> ORGANISM: Artificial Sequence
<220> FEATURE:
<223> OTHER INFORMATION: Chemically Synthesized - Primer

<400> SEQUENCE: 45
ccgcgtcctt gctctg                                                     16

<210> SEQ ID NO 46
<211> LENGTH: 13
<212> TYPE: DNA
<213> ORGANISM: Artificial Sequence
<220> FEATURE:
<223> OTHER INFORMATION: Chemically Synthesized - Primer

<400> SEQUENCE: 46
gggcccccgc gca                                                        13

<210> SEQ ID NO 47
<211> LENGTH: 5
<212> TYPE: PRT
<213> ORGANISM: Artificial Sequence
<220> FEATURE:
<223> OTHER INFORMATION: Chemically Synthesized - Zeta polypeptide

<400> SEQUENCE: 47

Tyr Trp His Ala Glx
1               5
```